US011123407B2

(12) United States Patent
Horcajada et al.

(10) Patent No.: US 11,123,407 B2
(45) Date of Patent: Sep. 21, 2021

(54) NUTRITIONAL COMPOSITION FOR TREATING OR PREVENTING IMPAIRED MOBILITY

(71) Applicant: NESTEC S.A., Vevey (CH)

(72) Inventors: Marie Noelle Horcajada, Echenevex (FR); Denis Breuille, Lausanne (CH); Claire Boutry, Perroy (CH); Zamzam Kabiry (Fariba) Roughead, Plymouth, MN (US)

(73) Assignee: Societe des Produits Nestle S.A., Vevey (CH)

( * ) Notice: Subject to any disclaimer, the term of this patent is extended or adjusted under 35 U.S.C. 154(b) by 196 days.

(21) Appl. No.: 16/303,471

(22) PCT Filed: May 24, 2017

(86) PCT No.: PCT/EP2017/062588
§ 371 (c)(1),
(2) Date: Nov. 20, 2018

(87) PCT Pub. No.: WO2017/202939
PCT Pub. Date: Nov. 30, 2017

(65) Prior Publication Data
US 2020/0316175 A1 Oct. 8, 2020

Related U.S. Application Data

(60) Provisional application No. 62/342,298, filed on May 27, 2016.

(51) Int. Cl.
| | |
|---|---|
| A61K 38/39 | (2006.01) |
| A61K 31/198 | (2006.01) |
| A61K 31/202 | (2006.01) |
| A61K 31/7048 | (2006.01) |
| A61K 31/728 | (2006.01) |
| A61K 31/737 | (2006.01) |
| A61K 31/12 | (2006.01) |
| A61K 31/355 | (2006.01) |
| A61K 31/375 | (2006.01) |
| A61K 31/593 | (2006.01) |
| A61K 33/04 | (2006.01) |
| A61K 33/06 | (2006.01) |
| A61K 33/30 | (2006.01) |
| A61K 35/66 | (2015.01) |
| A61K 36/16 | (2006.01) |
| A61K 36/21 | (2006.01) |
| A61K 36/258 | (2006.01) |
| A61K 36/41 | (2006.01) |
| A61K 36/87 | (2006.01) |

(52) U.S. Cl.
CPC .............. *A61K 38/39* (2013.01); *A61K 31/12* (2013.01); *A61K 31/198* (2013.01); *A61K 31/202* (2013.01); *A61K 31/355* (2013.01); *A61K 31/375* (2013.01); *A61K 31/593* (2013.01); *A61K 31/7048* (2013.01); *A61K 31/728* (2013.01); *A61K 31/737* (2013.01); *A61K 33/04* (2013.01); *A61K 33/06* (2013.01); *A61K 33/30* (2013.01); *A61K 35/66* (2013.01); *A61K 36/16* (2013.01); *A61K 36/21* (2013.01); *A61K 36/258* (2013.01); *A61K 36/41* (2013.01); *A61K 36/87* (2013.01)

(58) Field of Classification Search
CPC ...... A61K 38/39; A61K 31/12; A61K 31/198; A61K 31/202; A61K 31/355; A61K 31/375; A61K 31/593; A61K 31/7048; A61K 31/728; A61K 31/737; A61K 33/04; A61K 33/06; A61K 33/30; A61K 35/66; A61K 36/16; A61K 36/21; A61K 36/258; A61K 36/41; A61K 36/87; A61K 35/741; A61K 31/205; A61K 31/7008; A61K 45/06; A61P 43/00; A61P 3/02; A61P 25/28; A61P 21/00; A61P 19/10; A61P 19/08; A61P 19/02; A61P 19/00
See application file for complete search history.

(56) References Cited

FOREIGN PATENT DOCUMENTS

| WO | 2013017553 | 2/2013 |
|---|---|---|
| WO | 2014161872 | 10/2014 |
| WO | 2016044167 | 3/2016 |

OTHER PUBLICATIONS

Molfino et al., Nutrients, 2014, vol. 6, p. 4058-4072.*
Tieland et al., JAMDA, 2012, vol. 13, p. 713-719.*
Leong et al., Arthritis Research and Therapy, 2014,16:508, p. 1-11.*
Strike et al. "A High Omega-3 Fatty Acid Multinutrient Supplement Benefits Cognition and Mobility in Older Women: A Randomized, Double-blind, Placebo-controlled Pilot Study" J Gerontol A Biol Sci Med Sci, 2016, vol. 71, No. 2, pp. 236-242.

(Continued)

*Primary Examiner* — Kade Ariani
(74) *Attorney, Agent, or Firm* — K&L Gates LLP

(57) ABSTRACT

A method of treating or preventing impaired mobility in an older adult includes administering to the older adult an effective amount of a composition containing at least one ingredient for cognitive ability, at least one ingredient for muscle and/or bone quality, and at least one ingredient for joint quality and/or functionality. The older adult can be an elderly individual and/or can have a condition that is one or more of frailty, pre-frailty, sarcopenia, recovering from sarcopenia, malnutrition, at risk of malnutrition, undergoing rehabilitation, and being scheduled to undergo rehabilitation, disorders impacting mobility such as osteoporosis, osteoarthritis, pre-osteoarthritis, osteopenia, cognitive decline. In a non-limiting example of the composition, the at least one ingredient for muscle and/or bone quality and the at least one ingredient for joint quality include a protein source, omega-3 fatty acids, and a polyphenol.

17 Claims, No Drawings

(56) References Cited

OTHER PUBLICATIONS

Ogawa et al. "Eicosapentaenoic Acid Improves Glycemic Control in Elderly Bedridden Patients with Type 2 Diabetes" Tohoku J. Exp. Med., 2013, vol. 231, pp. 63-74.
Gupta et al. "Nutraceuticals for geriatrics" Journal of Traditional and Complementary Medicine, 2015, vol. 5, pp. 5-14.

\* cited by examiner

NUTRITIONAL COMPOSITION FOR TREATING OR PREVENTING IMPAIRED MOBILITY

CROSS REFERENCE TO RELATED APPLICATIONS

The present application is a National Stage of International Application No. PCT/EP2017/062588, filed on May 24, 2017, which claims priority to U.S. Provisional Patent Application No. 62/342,298, filed on May 27, 2016, the entire contents of which are being incorporated herein by reference.

BACKGROUND

The present disclosure generally relates to compositions and methods that improve mobility, for example in an older adult. More specifically, the present disclosure relates to compositions comprising at least one ingredient for cognitive ability, at least one ingredient for muscle and/or bone quality, and at least one ingredient for joint quality and further relates to methods comprising administering such compositions to an individual.

Mobility is the ability to move independently and safely from one place to another. Elderly individuals are at risk of frailty and dependence on assistance. Decreased mobility can arise from pain after physical activity, chronic low grade pain, a loss of energy (e.g., shortness of breath, rapid heart beating, muscular weakness, and/or becoming tired faster during physical activities such as sports or climbing stairs or ramps), and chronic joint pain. A variety of diseases and conditions are related to mobility, for example joint diseases, arthritis, rheumatic diseases, osteoarthritis, knee osteoarthritis, bone diseases, muscular diseases, metabolic bone diseases, osteoporosis, rheumatoid arthritis, and neuromuscular disorders.

However, the development of frailty is not necessarily inevitable. Appropriate advice and training of older adults can prevent many negative developments. The elderly can be assisted in maintaining or achieving an acceptable health status for a better quality of life. Nevertheless, previous approaches have not satisfactorily addressed the problem of impaired mobility.

SUMMARY

The present inventors noted that there is a gradual decrease in muscle function, capacity and reactivity with advancing age. For example, by 50 years of age, about 10% of muscle area is gone, and muscle strength declines by approximately 15% per decade in the ages of 60 and 70 years and by about 30% thereafter. Age-related decrease in muscle mass is responsible for almost all loss of strength and power in older adults, with an increase in fatigue. This decrease is due to inter-related factors: lifestyle, structural changes of the muscle, and metabolic changes.

The present inventors recognized this problem and addressed it by acting on all of the protein metabolism pathways at the same time; specifically, by using omega-3 fatty acids on insulin resistance, polyphenols on inflammation, and protein to promote protein synthesis. Managing insulin resistance and inflammation allows recovery of the anabolic effect of protein (managing the anabolic resistance. Furthermore, without being bound by theory, the present inventors believe that addressing the cognitive ability of the older adult, in combination with improving the muscle, bone and joint quality, synergistically improves the mobility of the older adult and related disorders.

Accordingly, in a general embodiment, the present disclosure provides a method of treating or preventing impaired mobility/mobility disorders in an older adult. The method comprises administering to the older adult an effective amount of a composition comprising at least one ingredient for cognitive ability, at least one ingredient for muscle and/or bone quality, and at least one ingredient for joint quality.

In an embodiment, the at least one ingredient for cognitive ability comprises an ingredient selected from the group consisting of omega-3 fatty acids, omega-6 fatty acids, phospholipids, lecithin, medium-chain triglycerides, ketone bodies, ketone esters, vitamin C, vitamin D, B vitamins, L-glutamine, L-phenylalanine, L-carnitine, creatine, citrulline, arginine, flavonoids, flavanols, polyphenols (e.g. curcumin, coffee or tea polyphenols, chlorogenic acid, catechins, epicatechins), zinc, selenium, magnesium, beetroot juice, concord grape juice, Ginkgo biloba, ginseng, *Rhodiola rosea*, a probiotic microorganism and combinations thereof.

In an embodiment, the at least one ingredient for muscle and/or bone quality comprises at least one ingredient for short-term muscle functionality. The at least one ingredient for short-term muscle functionality can comprise β-alanine or protein.

In an embodiment, the at least one ingredient for muscle and/or bone quality comprises at least one ingredient for long-term muscle quality and/or functionality. The at least one ingredient for long-term muscle quality and/or functionality can be selected from the group consisting of protein, amino acids, omega-3 fatty acids, creatine, carnitine, polyphenols (e.g. curcumin), citrulline and combinations thereof.

In an embodiment, the at least one ingredient for muscle and/or bone quality comprises at least one ingredient for bone quality. The at least one ingredient for bone quality can be selected from the group consisting of protein, vitamin C, vitamin D, vitamin E, vitamin K2, calcium, phosphorus, magnesium, zinc, polyphenols (e.g. hesperidin), probiotic microorganisms and combinations thereof.

In an embodiment, the at least one ingredient for joint quality comprises at least one ingredient for short-term joint quality and/or functionality. The at least one ingredient for short-term joint quality can be selected from the group consisting of glucosamine, chondroitin, hyaluronic acid and combinations thereof.

In an embodiment, the at least one ingredient for joint quality comprises at least one ingredient for long-term joint quality and/or functionality. The at least one ingredient for long-term joint quality can be selected from the group consisting of vitamin C, vitamin E, polyphenols (such as rutin, curcumin and/or oleuropein), omega-3 fatty acids, and combinations thereof.

In an embodiment, the at least one ingredient for joint quality and/or functionality comprises an ingredient selected from the group consisting of collagen, hydrolyzed collagen, polyphenols extracted from *Boswellia serrata* rose hip, and combinations thereof; preferably collagen and/or hydrolyzed collagen.

In a most preferred embodiment, the at least one ingredient for muscle and/or bone quality comprises an ingredient for muscle quality and/or functionality comprising protein from plant or animal source, the at least one ingredient for cognitive ability comprises omega-3 fatty acids, and the at least one ingredient for joint quality comprises a polyphenol (e.g., curcumin, rutin, and/or oleuropein). Preferably the omega-3 fatty acids and the polyphenol are administered in an amount that further provides a muscle and/or bone quality benefit from these compounds, and the protein source is administered in an amount that further provides a bone quality benefit from this compound. In a more preferred embodiment, the ingredients for muscle and/or bone quality, cognitive ability and joint quality consist of a source of whey protein, omega-3 fatty acids, and a polyphenol selected from curcumin, rutin and/or oleuropein.

In an embodiment, the older adult is an elderly individual.

In an embodiment, the older adult has a condition selected from the group consisting of frailty, pre-frailty, sarcopenia, recovering from sarcopenia, malnutrition, at risk of malnutrition, undergoing rehabilitation, scheduled to undergo rehabilitation, having disorders impacting mobility, or at risk of disorders impacting mobility, such as osteoporosis, osteoarthritis, pre-osteoarthritis, osteopenia, cognitive decline and combinations thereof.

In an embodiment, the composition is administered to the older adult at least one day per week for at least one month. The method can further comprise an exercise regimen performed by the older adult during the at least one month.

In another embodiment, the present disclosure provides a method of making a composition for treating or preventing impaired mobility in an older adult. The method comprises adding at least one ingredient for cognitive ability, at least one ingredient for muscle and/or bone quality, and at least one ingredient for joint quality to at least one other ingredient selected from the group consisting of a protein, a carbohydrate, a lipid, and a food additive. The food additive can be selected from the group consisting of acidulants, thickeners, buffers or agents for pH adjustment, chelating agents, colorants, emulsifiers, excipients, flavor agents, minerals, osmotic agents, a pharmaceutically acceptable carrier, preservatives, stabilizers, sugars, sweeteners, texturizers, vitamins, minerals and combinations thereof.

In another embodiment, the present disclosure provides a composition for treating or preventing impaired mobility/mobility disorders in an older adult, the composition comprising at least one ingredient for cognitive ability, at least one ingredient for muscle and/or bone quality, and at least one ingredient for joint quality.

An advantage of one or more embodiments provided by the present disclosure is to treat or prevent impaired mobility, such as age-related mobility loss and disorders impacting mobility such as osteoporosis, osteoarthritis, pre-osteoarthritis, osteopenia, cognitive decline.

Another advantage of one or more embodiments provided by the present disclosure is to flatten the slope of the decline from independent living to assisted living, thereby providing older adults with more years of independent living and a good quality of life.

Yet another advantage of one or more embodiments provided by the present disclosure is to address mobility disorders with a solution effective in the short, medium and long term.

Still another advantage of one or more embodiments provided by the present disclosure is to treat or prevent impaired mobility/mobility disorders using a nutritional solution.

An additional advantage of one or more embodiments provided by the present disclosure is to address impaired mobility using a cognitive approach in combination with an approach directed to muscle (e.g., promoting muscle mass and strength, decreasing muscle fatigue, ensuring muscle recovery after immobilization or disease), bone (e.g., limiting bone loss to maintain the quality and strength of the skeleton) and/or joint (e.g., preserving cartilage integrity and decreasing pain to ensure functionality).

Another advantage of one or more embodiments provided by the present disclosure is to use a food, food supplement, nutritional composition to assist a target population of elderly adults with self-diagnosed aging issues and individuals with pre-frailty such as elderly individuals with pre-osteoarthritis or at risk thereof. The food or food supplement can advantageously be provided through easily accessible channels such as retail outlets, for example supermarkets and pharmacies, and/or from an easily accessible source such as a healthcare provider, e.g., a pharmacist.

Yet another advantage of one or more embodiments provided by the present disclosure is to use a food for special medical purposes (FSMP) to assist a target population of individuals with pre-frailty and individuals with frailty such as elderly individuals who are malnourished or at risk thereof, individuals with sarcopenia or recovering from sarcopenia, and individuals undergoing rehabilitation or scheduled to undergo rehabilitation; individuals having disorders impacting mobility, or at risk of disorders impacting mobility, such as osteoporosis, osteoarthritis, pre-osteoarthritis, osteopenia, cognitive disorders and combinations thereof. The FSMP can advantageously be provided through institutions such as hospitals and nursing homes, and/or from a source such as a healthcare provider, e.g., a general practitioner, a specialist, or a dietician.

Another advantage of one or more embodiments provided by the present disclosure is to enhance health in an older adult to thereby promote freedom of movement, avoid pain after exercise, and improve quality of life.

Yet another advantage of one or more embodiments provided by the present disclosure is to maintain good health in an older adult by preventing low grade pain.

Still another advantage of one or more embodiments provided by the present disclosure is to address health threats by alleviating low grade pain and fatigue.

An additional advantage of one or more embodiments provided by the present disclosure is to alleviate discomforts of aging such as joint pain, a lack of energy, and decreased muscle mass/strength.

Another advantage of one or more embodiments provided by the present disclosure is to treat major health issues such as rehabilitation by promoting recovery of functionality and recovery of muscle mass/strength.

Additional features and advantages are described herein and will be apparent from the following Detailed Description.

DETAILED DESCRIPTION

All percentages expressed herein are by weight of the total weight of the composition unless expressed otherwise. As used herein, "about" is understood to refer to numbers in a range of numerals, for example the range of −10% to +10% of the referenced number, preferably −5% to +5% of the referenced number, more preferably −1% to +1% of the referenced number, most preferably −0.1% to +0.1% of the referenced number. All numerical ranges herein should be understood to include all integers, whole or fractions, within the range. Moreover, these numerical ranges should be construed as providing support for a claim directed to any number or subset of numbers in that range. For example, a disclosure of from 1 to 10 should be construed as supporting a range of from 1 to 8, from 3 to 7, from 1 to 9, from 3.6 to 4.6, from 3.5 to 9.9, and so forth.

As used in this disclosure and the appended claims, the singular forms "a," "an" and "the" include plural referents unless the context clearly dictates otherwise. Thus, for example, reference to "a component" or "the component" includes two or more components.

The words "comprise," "comprises" and "comprising" are to be interpreted inclusively rather than exclusively. Likewise, the terms "include," "including" and "or" should all be construed to be inclusive, unless such a construction is clearly prohibited from the context. Nevertheless, the compositions disclosed herein may lack any element that is not specifically disclosed herein. Thus, a disclosure of an embodiment using the term "comprising" includes a disclosure of embodiments "consisting essentially of" and "consisting of" the components identified.

The term "and/or" used in the context of "X and/or Y" should be interpreted as "X," or "Y," or "X and Y." Where used herein, the terms "example" and "such as," particularly when followed by a listing of terms, are merely exemplary and illustrative and should not be deemed to be exclusive or comprehensive. As used herein, "associated with" means occurring concurrently, preferably means caused by the same underlying condition, and most preferably means that one of the identified conditions is caused by the other identified condition.

"Prevention" includes reduction of risk and/or severity of a condition or disorder. The terms "treatment," "treat" and "to alleviate" include both prophylactic or preventive treatment (that prevent and/or slow the development of a targeted pathologic condition or disorder) and curative, therapeutic or disease-modifying treatment, including therapeutic measures that cure, slow down, lessen symptoms of, and/or halt progression of a diagnosed pathologic condition or disorder; and treatment of patients at risk of contracting a disease or suspected to have contracted a disease, as well as patients who are ill or have been diagnosed as suffering from a disease or medical condition. The term does not necessarily imply that a subject is treated until total recovery. The terms "treatment" and "treat" also refer to the maintenance and/or promotion of health in an individual not suffering from a disease but who may be susceptible to the development of an unhealthy condition. The terms "treatment," "treat" and "to alleviate" are also intended to include the potentiation or otherwise enhancement of one or more primary prophylactic or therapeutic measure. The terms "treatment," "treat" and "to alleviate" are further intended to include the dietary management of a disease or condition or the dietary management for prophylaxis or prevention a disease or condition. A treatment can be patient- or doctor-related.

The term "elderly" in the context of a human means an age from birth of at least 60 years, preferably above 63 years, more preferably above 65 years, and most preferably above 70 years. The term "older adult" in the context of a human means an age from birth of at least 45 years, preferably above 50 years, more preferably above 55 years, and includes elderly individuals.

"Sarcopenia" is defined as the age-associated loss of muscle mass and functionality (including muscle strength and gait speed).

"Cognitive ability" is defined as the intellectual process by which an individual becomes aware of, perceives, or comprehends ideas. Cognitive ability embraces the quality of knowing, which includes all aspects of perception, recognition, conception, sensing, thinking, reasoning, remembering and imaging. Loss of cognitive ability is the difficulty in dealing with or reacting to new information or situations. Cognitive impairment may manifest itself in many ways, e.g., short-term memory loss, diminished capacity to learn, diminished rate of learning, diminished attention, diminished motor performance, and/or dementia, among other indicia. Non-limiting examples of specific cognitive domains that include abilities that decrease with age are (i) attention: processing speed, and selected and divided attention; (ii) learning and memory: delayed free recall, source memory, prospective memory, and episodic memory; (iii) language: verbal fluency, visitation naming, and word finding; (iv) visuospatial abilities: visual construction skills; and (v) executive functioning: planning, decision making, reasoning, and mental flexibility.

"Muscle quality" comprises one or both of (i) muscle function or (ii) metabolic quality of skeletal muscle through fat infiltration. Muscle function is typically defined as strength per unit of appendicular skeletal muscle mass or per muscle volume. Non-limiting examples of ways to determine fat infiltration of muscle are computed tomography (CT) and magnetic resonance imaging (MRI).

"Malnutrition" is a condition in which the individual is consuming insufficient calories, protein and/or micronutrients. Malnutrition can be quantitatively determined using weight-for-height and/or height-for-age, as a specified percentage of the median. For example, mild malnutrition can be defined as 87.5-95% height-for-age relative to the median and/or 80-90% weight-for-height relative to the median; moderate malnutrition can be defined as 80-87.5% height-for-age relative to the median and/or 70-80% weight-for-height relative to the median; and severe malnutrition can be defined as less than 80% height-for-age relative to the median and/or less than 70% weight-for-height relative to the median.

As used herein, "frailty" is defined as a clinically recognizable state of increased vulnerability resulting from aging-associated decline in reserve and function across multiple physiologic systems such that the ability to cope with every day or acute stressors is compromised. In the absence of an established quantitative standard, frailty has been operationally defined by Fried et al. as meeting three out of five phenotypic criteria indicating compromised energetics: (1) weakness (grip strength in the lowest 20% of population at baseline, adjusted for gender and body mass index), (2) poor endurance and energy (self-reported exhaustion associated with VO2 max), (3) slowness (lowest 20% of population at baseline, based on time to walk 15 feet, adjusting for gender and standing height), (4) low physical activity (weighted score of kilocalories expended per week at baseline, lowest quintile of physical activity identified for each gender; e.g., less than 383 kcal/week for males and less than 270 kcal/week for females), and/or (5) unintentional weight loss (10 lbs. in past year). Fried L P, Tangen C M, Walston J, et al., "Frailty in older adults: evidence for a phenotype." J. Gerontol. A. Biol. Sci. Med. Sci. 56(3):M146-M156 (2001). A pre-frail stage, in which one or two of these criteria are present, identifies a high risk of progressing to frailty.

As used herein, an "effective amount" is an amount that prevents a deficiency, treats a disease or medical condition in an individual or, more generally, reduces symptoms, manages progression of the diseases or provides a nutritional, physiological, or medical benefit to the individual. The relative terms "improved," "increased," "enhanced" and the like refer to the effects of the composition disclosed herein (a composition comprising at least one ingredient for cognitive ability, at least one ingredient for muscle and/or bone quality, and at least one ingredient for joint quality)

relative to a composition lacking the ingredients for cognitive ability and muscle, bone and joint quality, but otherwise identical.

An aspect of the present disclosure is a method of treating or preventing impaired mobility in an older adult, the method comprising administering to the older adult an effective amount of a composition comprising at least one ingredient for cognitive ability, at least one ingredient for muscle and/or bone quality, and at least one ingredient for joint quality. The older adult can have a condition selected from the group consisting of frailty, pre-frailty, sarcopenia, recovering from sarcopenia, malnutrition, at risk of malnutrition, undergoing rehabilitation, scheduled to undergo rehabilitation (e.g., within the next year, preferably within the next six months, more preferably within the next month), disorders impacting mobility such as osteoporosis, osteoarthritis, pre-osteoarthritis, osteopenia, cognitive disorder and combinations thereof.

In some embodiments, the method increases the mobility in the older adult; for example, the mobility is greater after a time period of administration of the composition relative to immediately before administration began. In some embodiments, the method maintains mobility in the older adult; for example, the mobility is about the same after a time period of administration of the composition relative to immediately before administration began. In some embodiments, the method mitigates decreased mobility in the older adult; for example, after a time period of administration of the composition, the mobility is less than it was immediately before administration began but greater than the level it would have been had a composition lacking the ingredients for cognitive ability and muscle, bone and joint quality, but otherwise identical, been administered instead of the composition disclosed herein.

Another aspect of the present disclosure is a method of making a composition for treating or preventing impaired mobility in an older adult, the method comprising adding at least one ingredient for cognitive ability, at least one ingredient for muscle and/or bone quality, and at least one ingredient for joint quality to at least one other ingredient selected from the group consisting of a protein, a carbohydrate, a lipid, and a food additive.

Particularly preferred compositions are nutritional compositions, oral supplement, gels or liquid supplements, powdered nutritional compositions or supplement, nutraceutical, medical foods.

The composition can be in any oral nutritional form, e.g. as a health drink, as a ready-made drink, optionally as a soft drink, including juices, milk-shake, yogurt drink, smoothie or soy-based drink, in a bar, or dispersed in foods of any sort, such as baked products, cereal bars, dairy bars, snack-foods, soups, breakfast cereals, muesli, candies, tabs, cookies, biscuits, crackers (such as rice crackers), and dairy products.

The composition may be in the form of tablets, capsules, pastilles or a liquid, for example. The composition may further contain protective hydrocolloids (such as gums, proteins, modified starches), binders, film forming agents, encapsulating agents/materials, wall/shell materials, matrix compounds, coatings, emulsifiers, surface active agents, solubilizing agents (oils, fats, waxes, lecithins or the like), adsorbents, carriers, fillers, co-compounds, dispersing agents, wetting agents, processing aids (solvents), flowing agents, taste masking agents, weighting agents, jellifying agents and gel forming agents.

In an embodiment, the protein source may be dietary protein including, but not limited to animal protein (such as milk protein, meat protein or egg protein), vegetable protein (such as soy protein, wheat protein, rice protein, and pea protein), or combinations thereof. In an embodiment, the protein is selected from the group consisting of whey, chicken, corn, caseinate, wheat, flax, soy, carob, pea or combinations thereof.

In an embodiment, vegetable proteins can be used. Based on the nutritional profile of specific vegetable proteins (e.g., pea protein isolate) there are limitations in the amount of vegetable protein sources that can be included in a formula. For example, the amino acid profile of pea protein includes all of the indispensable amino acids. Pea protein is relatively rich in arginine, but limiting in the sulphur-containing amino acids, methionine, and cysteine. However, it is possible, for example, to blend pea protein isolates with a complete protein source (such as milk protein or complete vegetable proteins) having sufficient sulphur-containing amino acids to offset such deficiency. Canola protein (i.e., isolates, hydrolysates and concentrates) is one such vegetable protein which can provide appreciable amounts of sulfur-containing amino acids to further augment the amino acid profile to deliver the necessary protein quality to the patient. Additionally, animal derived proteins are typically more abundant in sulphur-containing amino acids than vegetable proteins.

The compositions of the present disclosure may also include a source of carbohydrates. Any suitable carbohydrate may be used in the present nutritional compositions including, but not limited to, sucrose, lactose, glucose, fructose, corn syrup solids, maltodextrin, modified starch, amylose starch, tapioca starch, corn starch or combinations thereof.

A source of fat may also be included in the present compositions. The source of fat may include any suitable fat or fat mixture. For example, the fat source may include, but is not limited to, vegetable fat (such as olive oil, corn oil, sunflower oil, high-oleic sunflower, flax seed oil, rapeseed oil, canola oil, high oleic canola oil, hazelnut oil, soy oil, palm oil, coconut oil, blackcurrant seed oil, borage oil, lecithins, and the like), animal fats (such as milk fat), or combinations thereof. The source of fat may also be less refined versions of the fats listed above (e.g., olive oil for polyphenol content).

In an embodiment, the compositions further include one or more prebiotics. Non-limiting examples of prebiotics include acacia gum, alpha glucan, arabinogalactans, beta glucan, dextrans, fructooligosaccharides, fucosyllactose, galactooligosaccharides, galactomannans, gentiooligosaccharides, glucooligosaccharides, guar gum, inulin, isomaltooligosaccharides, lactoneotetraose, lactosucrose, lactulose, levan, maltodextrins, milk oligosaccharides, partially hydrolyzed guar gum, pecticoligosaccharides, resistant starches, retrograded starch, sialooligosaccharides, sialyllactose, soyoligosaccharides, sugar alcohols, xylooligosaccharides, their hydrolysates, or combinations thereof.

The compositions may further include one or more probiotics. Non-limiting examples of probiotics include *Aerococcus*, Aspergillus, *Bacteroides, Bifidobacterium*, Candida, *Clostridium*, Debaromyces, *Enterococcus, Fusobacterium, Lactobacillus, Lactococcus, Leuconostoc, Melissococcus, Micrococcus*, Mucor, *Oenococcus, Pediococcus*, Penicillium, Peptostrepococcus, Pichia, *Propionibacterium*, Pseudocatenulatum, Rhizopus, Saccharomyces, *Staphylococcus, Streptococcus*, Torulopsis, *Weissella*, non-replicating microorganisms, or combinations thereof.

The food additive can be selected from the group consisting of acidulants, thickeners, buffers or agents for pH adjustment, chelating agents, colorants, emulsifiers, excipients, flavor agents, minerals, osmotic agents, a pharmaceutically acceptable carrier, preservatives, stabilizers, sugars, sweeteners, texturizers, vitamins, minerals and combinations thereof.

The compositions of the present disclosure may be a source of either incomplete or complete nutrition. The nutritional compositions may be administered by oral administration or tube feeding. If the nutritional compositions are formulated to be administered orally, the compositions may be a liquid oral nutritional supplement or feeding. The nutritional compositions may also be used for short term or long term tube feeding.

In an embodiment, the composition is administered to the individual for a time period of at least one month; preferably at least two months, more preferably at least three, four, five or six months; most preferably for at least one year. During the time period, the composition can be administered to the individual at least one day per week; preferably at least two days per week, more preferably at least three, four, five or six days per week; most preferably seven days per week. The composition can be administered in a single dose per day or in multiple separate doses per day.

The composition for treating or preventing impaired mobility in an older adult according to the present invention comprises at least one ingredient for cognitive ability, at least one ingredient for muscle and/or bone quality, and at least one ingredient for joint quality.

Preferably the at least one ingredient for cognitive ability improves, or mitigates loss of, cognitive ability. Non-limiting examples of suitable ingredients for cognitive ability include *Ginkgo biloba*, ginseng, *Rhodiola rosea*, phospholipids (e.g., phosphatidylserine and phosphatidylcholine), lecithin, L-glutamine, L-phenylalanine, magnesium (e.g., magnesium L-threonate), B vitamins, flavonoids and flavanols from all sources (e.g., from cocoa), omega-3 fatty acids, omega-6 fatty acids, L-carnitine, creatine, medium-chain triglycerides (MCTs), ketone bodies, ketone esters, polyphenols (e.g., resveratrol), antioxidants (e.g., vitamin C and selenium), nitric oxide releasing compounds (e.g., citrulline and arginine), polyphenols (e.g. coffee or tea polyphenols, chlorogenic acid, catechins, epicatechins, curcumin), vitamin D, zinc (e.g., zinc citrate trihydrate), beetroot juice, concord grape juice (which has both pre-clinical and clinical data on cognition), probiotic microorganism and combinations thereof.

Preferably the at least one ingredient for muscle and/or bone quality and/or functionality improves, or mitigates loss of, both muscle quality and/or functionality and bone quality. For example, the composition can comprise an ingredient that provides both of these effects (e.g., an ingredient for muscle quality and bone quality) and/or multiple ingredients that individually provide both of these effects (e.g., a first ingredient for muscle quality and a second ingredient for bone quality). In an embodiment, the at least one ingredient for muscle and/or bone quality comprises at least one ingredient for short-term muscle functionality, for example β-alanine, protein and/or at least one ingredient for long-term muscle quality and/or functionality, for example protein, omega-3 fatty acids, a polyphenol, or combinations thereof. Non-limiting examples of other suitable ingredients for muscle quality and/or functionality include protein, amino acids, omega-3 fatty acids, creatine, carnitine, polyphenols (e.g. curcumin), citrulline acai (supports maintenance of exercise capacity), sources of naturally-occurring nitrates that facilitate blood flow via vessel relaxation (e.g., beet root or beet root juice), and combinations thereof.

Preferably the at least one ingredient for muscle and/or bone quality comprises at least one ingredient for bone quality, for example protein, vitamin C, vitamin D, vitamin K2, calcium, phosphorus, magnesium, zinc, polyphenols (e.g. hesperidin (flavanone)), probiotic microorganisms and combinations thereof.

Preferably the at least one ingredient for joint quality and/or functionality improves, or mitigates loss of, joint quality and/or functionality. In an embodiment, the at least one ingredient for joint quality comprises at least one ingredient for short-term joint quality, for example, glucosamine (e.g., glucosamine sulfate), chondroitin (e.g., chondroitin sulfate), hyaluronic acid (e.g., a rooster comb extract rich in hyaluronic acid) or combinations thereof (preferably at least hyaluronic acid), and/or at least one ingredient for long-term joint quality, for example vitamin C, vitamin E, polyphenols such as oleuropein, curcumin and rutin; omega-3 fatty acids, or combinations thereof. Non-limiting examples of other suitable ingredients for joint quality include collagen, hydrolyzed collagen, polyphenols extracted from *Boswellia serrata*, rose hip, and combinations thereof.

In a non-limiting example of the composition, the at least one ingredient for muscle and/or bone quality and the at least one ingredient for joint quality include a protein source, omega-3 fatty acids, and a polyphenol, more preferably curcumin, rutin and/or oleuropein.

A "polyphenol" is a compound comprising an aromatic ring bearing one or more hydroxy substituents, including functional derivatives. Non-limiting examples of suitable polyphenols are flavonoids such as isoflavones, anthocyanins, proanthocyanidins and anthocyanidins, flavans, flavonols, flavones and flavanones. Specific examples of flavonoids are catechins (catechin, epicatechin, gallocatechin, epigallocatechin, epicatechin gallate, epigallocatechin gallate), oleuropein, quercetin, rutin, curcumin, hesperidin and genistein.

The protein can be whey, e.g., native whey, intact unhydrolyzed whey, whey protein concentrate, whey protein isolate, acid whey, sweet whey, modified sweet whey (sweet whey from which the caseino-glycomacropeptide has been removed), a fraction of whey protein, or whey protein hydrolysate; casein; a vegetable protein such as soy protein, pea protein, potato protein, rice protein; and combinations thereof. The casein may be provided in free form or in the form of a salt, for example, a sodium salt, a calcium salt or a potassium salt. Although the protein can comprise vegetable protein, in some embodiments the composition is gluten-free.

The protein may be extensively hydrolyzed protein hydrolysates prepared from acid or enzyme treated animal and vegetable proteins, such as casein hydrolysate, whey hydrolysate, casein/whey hydrolysate, soy hydrolysate, and mixtures thereof "Extensively hydrolyzed" protein hydrolysates means that the intact protein is hydrolyzed into peptide fragments in which a majority of the peptide fragments have a molecular weight less than 1,000 Daltons, preferably at least about 75% and most preferably at least about 95% of the peptide fragments having a molecular weight less than about 1,000 Daltons. Free amino acids and synthetic short peptide chains may be substituted for or added to the protein hydrolysates.

In an embodiment, the protein comprises whey protein micelles as described in U.S. Patent App. Pub. No. 2009/0035437 where they are referred to as WPM.

In an embodiment, the method includes an exercise regimen for the individual, for example one or more of endurance training or resistance training. In another embodiment, the individual does not perform an exercise regimen. An example of endurance training is 30-60 minutes of moderate intensity activity per day, in bouts of at least 10 minutes each, for several days per week to total 150-300 minutes/week. Another example of endurance training is 20-30 minutes of vigorous intensity activity per day for several days per week to total 75-150 minutes/week). An example of resistance training is a progressive weight training program or weight-bearing calisthenics (8-10 exercises involving the major muscle groups of 8-12 repetitions each), stair climbing, and other strengthening activities that use the major muscle groups, at least two days per week.

It should be understood that various changes and modifications to the presently preferred embodiments described herein will be apparent to those skilled in the art. Such changes and modifications can be made without departing from the spirit and scope of the present subject matter and without diminishing its intended advantages. It is therefore intended that such changes and modifications be covered by the appended claims.

The invention is claimed as follows:

1. A method of treating or preventing impaired mobility in an older adult, the method comprising administering to the older adult an effective amount of a composition comprising at least one ingredient for cognitive ability, at least one ingredient for muscle and/or bone quality, and at least one ingredient for joint quality,
wherein the at least one ingredient for muscle and/or bone quality comprises an ingredient for muscle quality and/or functionality comprising a protein source, the at least one ingredient for cognitive ability comprises omega-3 fatty acids, and the at least one ingredient for joint quality comprises a polyphenol.

2. The method of claim 1, wherein the at least one ingredient for cognitive ability further comprises omega-6 fatty acids and B vitamins.

3. The method of claim 1, wherein the at least one ingredient for muscle and/or bone quality further comprises at least one ingredient for short-term muscle functionality.

4. The method of claim 3, wherein the at least one ingredient for short-term muscle functionality comprises β-alanine.

5. The method of claim 1, wherein the at least one ingredient for muscle and/or bone quality further comprises at least one ingredient for bone quality.

6. The method of claim 5, wherein the at least one ingredient for bone quality comprises vitamin D, vitamin E, and calcium.

7. The method of claim 1, wherein the at least one ingredient for joint quality further comprises at least one ingredient for short-term joint quality and/or functionality.

8. The method of claim 7, wherein the at least one ingredient for short-term joint quality and/or functionality is selected from the group consisting of glucosamine, chondroitin, hyaluronic acid and combinations thereof.

9. The method of claim 1, wherein the at least one ingredient for joint quality further comprises an ingredient selected from the group consisting of collagen, hydrolyzed collagen, and combinations thereof.

10. The method of claim 1, wherein the older adult is an elderly individual.

11. The method of claim 1, wherein the older adult has a condition selected from the group consisting of frailty, pre-frailty, sarcopenia, recovering from sarcopenia, malnutrition, at risk of malnutrition, undergoing rehabilitation, scheduled to undergo rehabilitation, disorders impacting mobility, and combinations thereof.

12. The method of claim 1, wherein the composition is administered to the older adult at least one day per week for at least one month.

13. The method of claim 12, further comprising an exercise regimen performed by the older adult during the at least one month.

14. The method of claim 1, wherein the polyphenol is selected from the group consisting of curcumin, chlorogenic acid, catechin, epicatechin, hesperidin, rutin, oleuropein, coffee polyphenol, tea polyphenol, and mixtures thereof.

15. The method of claim 1, wherein the protein source is a source of whey protein.

16. The method of claim 1, wherein the polyphenol is selected from the group consisting of curcumin, rutin, oleuropein, and mixtures thereof.

17. The method of claim 1, wherein the at least one ingredient for muscle and/or bone quality consists of the protein source, and the protein source is a source of whey protein; the at least one ingredient for cognitive ability consists of the omega-3 fatty acids; and the at least one ingredient for joint quality consists of the polyphenol, and the polyphenol is selected from the group consisting of curcumin, rutin, oleuropein, and mixtures thereof.

* * * * *